United States Patent [19]
Wendt et al.

[11] Patent Number: 4,510,933
[45] Date of Patent: Apr. 16, 1985

[54] SUCTION ADAPTER AND MEDICAL DRAINING SET AND METHOD OF USING A TRACHEAL DRAINING DEVICE

[75] Inventors: Michael Wendt, Münster-Nienberge; Erik Schwanbom, Lübeck, both of Fed. Rep. of Germany

[73] Assignee: Drägerwerk Aktiengesellschaft, Fed. Rep. of Germany

[21] Appl. No.: 494,526

[22] Filed: May 13, 1983

[30] Foreign Application Priority Data

Jun. 16, 1982 [DE] Fed. Rep. of Germany ...... 3222539

[51] Int. Cl.³ .......................................... A61M 16/00
[52] U.S. Cl. .............................. 128/207.14; 128/912; 604/167
[58] Field of Search .................. 128/200.26, 207.14, 128/207.15, 207.16, 912, 4, 204.18, 6; 604/164, 167, 169, 256

[56] References Cited

U.S. PATENT DOCUMENTS

| 555,588 | 3/1896 | Spencer | 604/247 |
|---|---|---|---|
| 1,089,805 | 3/1914 | Wolf | 604/99 |
| 2,915,063 | 12/1959 | Cutter | 604/163 |
| 3,902,500 | 9/1975 | Dryden | 128/207.14 |
| 4,233,982 | 11/1980 | Bauer et al. | 604/169 |
| 4,416,273 | 11/1983 | Grimes | 128/207.15 |

FOREIGN PATENT DOCUMENTS

| 216569 | 3/1958 | Australia | 128/207.14 |
|---|---|---|---|
| 1174394 | 12/1969 | United Kingdom | 128/207.14 |

*Primary Examiner*—Henry J. Recla
*Attorney, Agent, or Firm*—McGlew and Tuttle

[57] ABSTRACT

A suction adapter for connecting a suction cathetor to a tracheal tube which is also connected to a respirator comprises a hollow body which has a first opening with a tracheal tube receiver fitting, a second opening with a respirator line connector and a third opening for introducing a suction catheter which is advantageously aligned with the tracheal tube receiver fitting. The hollow body or connector includes a first valve which closes the outside of the third opening and it includes a valve member which may be stopped in a closed as well as in an opened position. The second valve member is located within the hollow body and is spaced from the outside or first valve member. A passage in the interior of the hollow body is defined between the two valve members and the second valve member includes a valve seat at the end of the passage and a valve member which is pivotally mounted in the body which is engageable on the valve seat to close the passage. This second valve member is urged by a spring into a closing position. In accordance with the method of the invention, when the suction catheter is to be introduced into the fitting, the catheter housed in a casing of plastic is connected to the fitting by the insertion of a stop sleeve member after the member has been freed from the plastic. A catheter tube enclosed in the plastic is inserted through the stop sleeve and into the fitting after the first valve member is in the opened position. The stop sleeve contacts the inner valve or second valve and the amount of the insertion of the stop sleeve is controlled by knurls formed on the outside of the stop sleeve. A catheter tube is pushed through its plastic coating and through the stop sleeve and it is connected at its opposite end to a source of suction after first removing a plastic covering from this end of the tube. After the drainage is effected the catheter tube is withdrawn into its enclosing plastic so that no contamination of the outside atmosphere is possible.

15 Claims, 3 Drawing Figures

SUCTION ADAPTER AND MEDICAL DRAINING SET AND METHOD OF USING A TRACHEAL DRAINING DEVICE

FIELD AND BACKGROUND OF THE INVENTION

This invention relates in general to medical devices particularly for drainage of a tracheal tube and to a new and useful suction adapter and medical draining set into a method of using the same.

In general, the patient under respiratory treatment is connected to a respirator through a suction adapter which is provided between the respirator line and an endotracheal tube and serves as a device for introducing the suction catheter.

As soon as, in order to introduce the suction catheter, the respiration is interrupted, there is a hazard, particularly under a respiration with a positive end expiratory pressure, that larger amounts of un-oxygenated blood will suddenly enter the arterial branch of the blood carrying system. A following acute volume load on the left heart portion and a supply with not oxygenated, venous blood frequently leads to a bradycardia, under adverse circumstances even to a stop of the heart. Consequently, what is required is a suction adapter which makes it possible to introduce the suction catheter without interrupting the respiration.

In German OS No. 23 08 400, an endotracheal respiratory tube is shown with an introduced catheter for continuous draining by suction. In an upper part of the device, an outer flap valve is provided for introducing the catheter, and two inner superjacent flap valves of rubber are mounted in a pipe connection.

The suction catheter advanced through the inlet opening thus penetrates an elastic outer seal and an inner seal and can be employed for continuously draining the bronchial secretion under simultaneous respiration.

Another suction adapter for endotracheal tubes for draining under continuous respiration is shown in the German periodical "Anaesthesist" 1981, pages 533–534 in an article by Ch. Spiss, W. Mauritz and P. Sporn. This suction adapter which is connectable to the respirator line and the tube is designed with a lateral, toothed slide for exposing an opening in the side wall, through which a suction catheter can be introduced.

The prior art suction adapters are effective in preventing the respirator line from being disconnected, and thus avoiding special hazards due to hemodynamics. With a positive end expiratory pressure respiration (PEEP), however, a substantial pressure drop during the draining operation cannot be prevented. In addition, they do not ensure sterile conditions with regard to the patient, sometimes not even with regard to the ambience.

The invention is directed to a development of an adapter of the above mentioned kind, permitting in a PEEP method to substantially maintain the pressure even during the suctorial draining operation, and ensuring a sterile manipulation. Further, under conditions of fouling, the adapter must be easy to clean, and it must be inexpensive in series manufacture.

In accordance with the invention there is provided a suction adapter for connecting a suction catheter to a tracheal tube which is also connected to a respirator and which comprises a hollow body or fitting which has a first opening with a tracheal tube receiving fitting. The hollow body also includes a second opening with a respirator line connector and a third opening which is advantageously aligned with the tracheal tube opening for introducing a suction catheter. The first or outer valve 10 closes the third opening and it includes a valve lid member which may be stopped in a completely closed or completely open position. The second or inner valve member is located within the hollow body and is spaced from the first valve member and defines a passage between the first and second valve members. The second valve member has a valve seat located within the body and a valve member which is pivotally mounted within the body which is biased by the spring into a closed position. The inner valve member or second valve member is located so that the catheter tube may be inserted through the third opening after the lid is positioned in an opened position and a stop sleeve thereof may be pushed in through the passage to open the inner valve to permit the cathether tube to be pushed through the stop sleeve into the fitting.

To facilitate the removal of the inner lid made entirely of plastic, it may be adviseable to provide the lid with an about H-shaped punched recess on the side facing outwardly when the lid is in closed position. Then, with the aid of a metallic bolt provided with a corresponding H-shaped elevation, and with the lid properly held fast from the opposite side, the journals can be pushed out of their bearing recesses. After cleaning, for example, the lid can be inserted again by simply pushing the journals into their bearing recesses.

It is advisable to make the outer lid arrestable in both the closed and open positions thereof, for example by snapping into retaining elements of corresponding shape.

In an advantageous development, the tubular catheter part may be provided on its proximal end with a connecting part for the suction line. This part is also enclosed in a tear-open casing of plastic which may in addition be filled with a disenfecting, protective gas.

Due to this provision of different casings of plastic, to be torn open separately, the catheter can be handled in a sterile manner, as explained hereinafter. Instead of plastic, the casings might also be made of another material of equivalent properties, such as thin metallic foil.

The claimed features make sure that the inventive adapter can be well handled, that it will be reliable in operation even under unclean conditions, and will be easy to clean and disinfect. A draining set comprising this suction adapter permits a virtually completely sterile introduction and withdrawal of the catheter.

Accordingly, it is an object of the invention to provide an improved suction adapter for connecting a suction catheter to a tracheal tube which is also connectable to a respirator. A further object of the invention is to provide a medical draining set which includes a catheter tube and a stop sleeve which are arranged within a closed plastic covering and in a manner such that the tube may be pushed through the stop sleeve after the sleeve is inserted into the fitting which has an outer valve and an inner valve which may be pressed opened after insertion of the stop sleeve.

A further object of the invention is to provide a method of draining a tracheal tube connection which comprises maintaining a catheter tube in a plastic covering, fitting a stop sleeve to a fitting for the tube and inserting the tube through the stop sleeve as it is moved out of the plastic covering, connecting the opposite end of the tube to a suction source, and after applying suction and draining the tracheal tube to withdraw the tube through the stop sleeve into the plastic covering.

A further object of the invention is to provide a suction adapter which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 2:
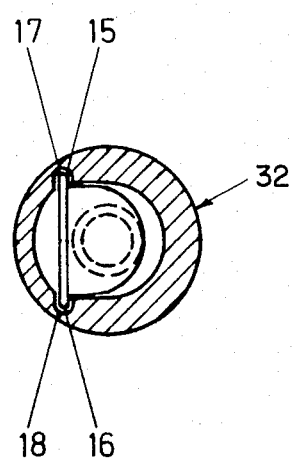
FIG. 2 is a section taken along the line A—A of FIG. 1.

Referring to the drawings in particular the invention embodied therein comprises a suction adapter generally designated 32 which comprises a hollow body or fitting 34 having a valve part 2 and an air conducting part 1. In accordance with the invention the adapter 32 has a first opening 36 with a tracheal tube receiving fitting for receiving an intermediate piece 5 connected to one end of tracheal tube 4. The adapter 32 includes a second opening 38 with a respirator line connector 8 and a third opening 39 for introducing a suction catheter generally designated 40 as shown in FIG. 3.

In accordance with the invention a first or outer valve comprises a lid 10 for closing the third opening 39 which may be stopped in a position completely closing the opening or completely opening the opening. The construction includes a second valve or interior valve which is located within the hollow body and spaced from and aligned with the first valve. A passage 9 is defined between the first and second valves at the entrance to the interior of the hollow body. The second valve includes a valve seat within the body and a valve member 11 which is pivotally mounted in the body and is engageable on the valve seat to close the passage. Spring means in the form of a coil spring 12 urges the valve member 11 to a closed position. The force of this spring may be overcome by inserting a stop sleeve member 19 of a catheter tube set 40.

Figure 3:
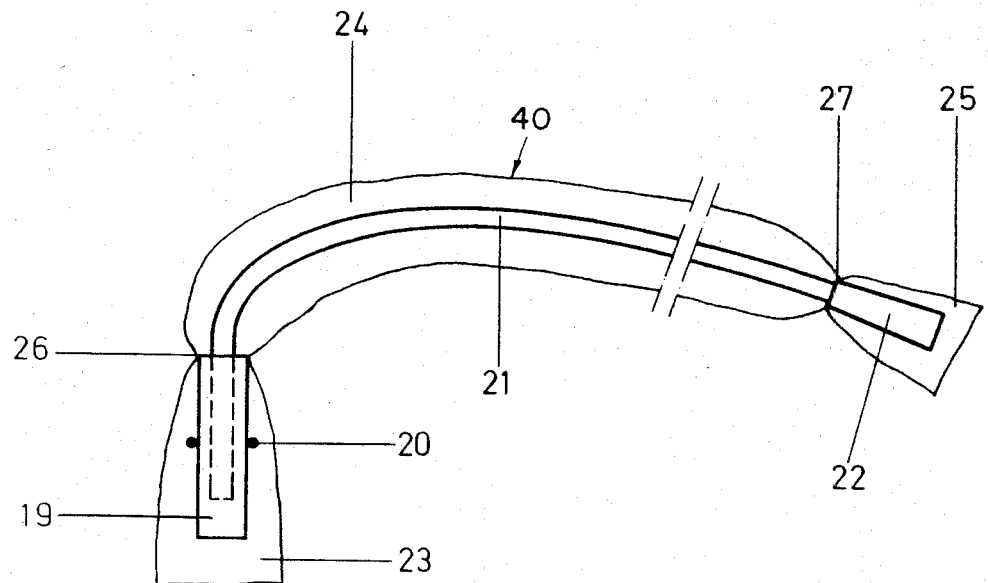
FIG. 3 is a side elevational view of a suction catheter usable in connection with the adapter shown in FIGS. 1 and 2.

As shown in FIG. 3, the catheter tube set 40 includes stop sleeve which may be inserted through the introductary passage 9 after the lid 10 is opened to the limit of stop knurls 20 which are defined on the exterior of the stop sleeve. The stop sleeve is initially packaged in a plastic coating 23 which is connected to another plastic coating 24 which covers a catheter part or tube 21. The tube 21 in turn is enclosed by a plastic casing 24 which is gathered at a fixing zone 27 and a separate plastic covering 25 covers a connecting part 22 of the tube and permits this tube to be connected to a suction source (not shown). After the stop sleeve is inserted into the introductory passage 9 and opens the valve member 11 the catheter tube part 21 may be pushed through the stop sleeve and the opposite connecting part 22 connected to the suction source and the tracheal tube 4 may thus be drained. Catheter part 21 is pulled back into the plastic casing 24 after drainage and thus none of the parts will contaminate the exterior atmosphere.

Figure 1:
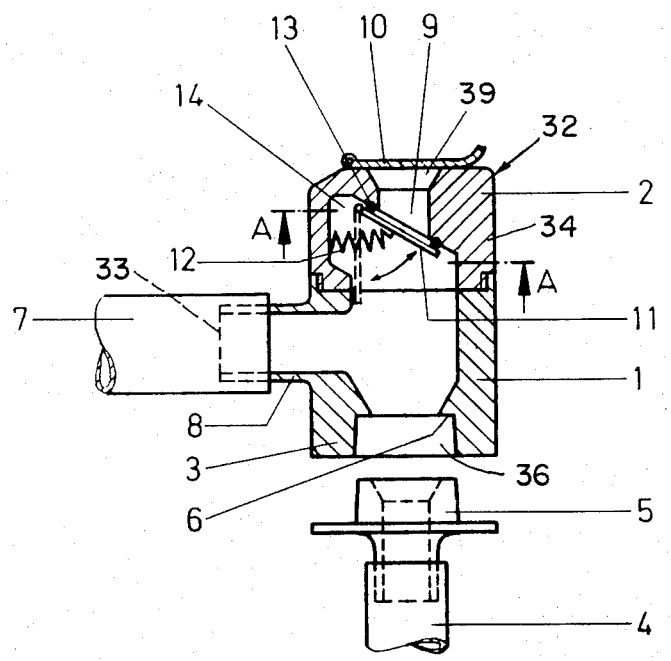
FIG. 1 is a longitudinal sectional view of an adapter for facilitating draining of a tracheal tube constructed in accordance with the invention.

As shown in FIGS. 1 and 2, the housing of the adapter comprises an air conducting part 1 which is screwed to a valve part 2.

Air conducting part 1 has an extension 3 into which an endotracheal tube 4 can be introduced, with the interposition of an intermediate piece 5. The opening 20 which is provided for this purpose is designed with a stop ledge 6 having its inside surface extending obliquely to the interior of the housing.

The width of the ledge surface facing the outside is equal to at least the wall thickness of tube 4, or of intermediate piece 5, so that a secure guidance of the catheter is achieved. Air conducting part 1 has further an extension 8 serving as a connection for the flexible tube 7 of the respirator (not shown).

Valve part 2 is designed with an introductory passage 9 having a conically flaring inlet portion. Introductory passage 9 is closable by an outer lid 10 which can be arrested in both its closing and opening position.

At the other end of passage 9, in the interior of parts 2, an inner lid 11 is pivotally mounted and urged into its closing position by a biased helical compression spring 12. The seat of lid 11 extends obliquely and is formed by a rubber-elastic seal ring 13. Spring 12 extends in a receiving space 14 which is dimensioned for accommodating inner lid 11 in the open position thereof into which it is pushed by an introduced catheter (not shown in FIG. 2).

As shown in FIG. 2, inner lid 11 has a contour in the shape of a segment of a circle and is seated, through journal portions 15, 16, in corresponding bearing recesses 17, 18 of valve part 2.

A suction catheter 30 to be used with the adapter comprises, according to FIG. 3, a stop sleeve 19 which is conformable to introductory passage 9 of the adapter and provided with stop knurls 20 limiting the depth of introduction. Through the stop sleeve 19, a tubular catheter part 21 can be advanced as needed. This part 21 carries a connecting part 22 on its proximal end, through which the catheter is to be connected to a low-pressure suction line. Stop sleeve 19, tubular part 21, and connecting part 22 are enclosed in separate plastic casings, 23, 24, 25 to be torn open and having common fixing zones 26, 27 in the zone of the proximal end of stop sleeve 19, and at the joint between the connecting part and the tubular part.

In use, first the outer lid 10 of the adapter is arrested in its open position. Then, the suction catheter 30 equipped according to FIG. 3 is prepared by tearing open plastic casing 25 enclosing connecting part 22. After establishing connection with the suction line, tubular part 21 is kinked, to prevent any flow of gas therethrough. Thereupon, plastic casing 23 enclosing stop sleeve 19 is torn open and the sleeve is engaged into introductory passage 9 of valve part 2 until knurls 20 stop the advance. Inner lid 11 is thereby opened.

The tubular part 21 of the catheter, upon being stretched, can now be pushed forward to start the draining. Upon terminating the operation, tubular part 21 is retracted into plastic casing 24. Only then, stop sleeve 19 is withdrawn from introductory passage 9. Tubular part 21 which now may be contaminated, is thus received in plastic casing 24 and can be removed without affecting the ambience with contamination.

While specific embodiments of the invention have been shown and described in detail to illustrate the application of the principles of the invention, it will be understood that the invention may be embodied otherwise without departing from such principles.

What is claimed is:

1. A suction adapter for connecting a suction catheter to a tracheal tube and which is also adapted to be connected to a respirator, comprising a hollow body having a first opening with a tracheal tube receiving fitting, a second opening having a respiratory line connection, and a third opening defining a drainage catheter introductory passage, the interior of said body defining a flow passage having a larger cross-section than said introductory passage and fluidically connecting said first opening and said third opening and fluidically connected to said second opening, the interior of said body defining a valve seat between the introductory passage and said flow passage, a valve member pivotally mounted in said body and engageable with said valve seat to close said introductory passage, spring means urging said valve member into engagement with said seat, a catheter assembly including a suction catheter having first and second end portions and a stop sleeve and means for slidably mounting said stop sleeve over said first end portion of said suction catheter, said stop sleeve having first and second ends and an exterior cross-section substantially the same as the cross-section of said introductory passage whereby said stop sleeve is slidably mounted therein with said first and extending into said flow passage, said stop sleeve also being provided with an exterior radially outwardly extending knurling at a spaced location from said first end thereof wider than said introductory passage such that when said stop sleeve is inserted into the said introductory passage up to said knurling, said first thereof forces said valve member back away from said seat.

2. A suction adapter according to claim 1, including a plastic cover extending over said stop sleeve and said catheter tube and being fixed to said sleeve at said second end thereof and to said tube at said second end portion thereof and extending beyond the ends of each of said sleeve and said tube, said cover being engageable to handle said suction catheter to insert it in said hollow body and to thereafter remove it without contaminating the surrounding space.

3. A suction adapter according to claim 2, including a separate tear-opening plastic covering said connecting end of said catheter tubular part and said stop sleeve as well as said catheter tubular part.

4. A suction adapter according to claim 2, including a connection on said catheter tube for connecting said tube to a suction supply and a separate tear-opened plastic covering each of said connecting parts, said catheter tube and said stop sleeve and isolating each of these parts.

5. A suction adapter according to claim 1, wherein said valve seat extends obliquely in respect to the longitudinal axis of said introductory passage, said valve body including a space at one side of said seat accommodating said valve member and it is pushed back away from said seat upon insertion of a catheter.

6. A suction adapter according to claim 1, wherein said valve member has a shape of a segment of a circle.

7. A suction adapter according to claim 1, including a stop ledge defined around said first opening, said valve body having an extension portion extending beyond said ledge, the interior of said body on the opposite side of said extension from said ledge being oblique.

8. A suction adapter according to claim 1, wherein said seat includes a rubber-elastic seal ring.

9. A suction adapter according to claim 1, wherein said valve member comprises a plastic member having a rear portion with laterally extending journal at each side rotatably mounted at said housing.

10. A suction adapter according to claim 1, including means arresting said first valve in an open position and in a closed position.

11. A suction adapter according to claim 1, including a separate plastic covering over each of said stop sleeve and said catheter tube.

12. A set according to claim 11, wherein said connecting part has a separate plastic covering as does said stop sleeve, each of which are made with a tear-opening permitting them to be opened, said catheter tube being sealed within the area between said stop member and said connection for a suction.

13. A method of draining a tracheal tube which is connected to a respirator by a connector having a through-passage comprising providing a suction port in said connector fluidically communicating with said through-passage, providing an interior valve in said through-passage located and biased to close said suction port, providing an exterior valve on said connector located to close said suction port and which is openable outwardly of said suction port and using a catheter assembly including a stop sleeve which is insertable in the suction port and a catheter tube which is slidably insertable into the stop sleeve and including a plastic cover second around both the catheter tube and the stop sleeve comprising inserting the stop sleeve into the suction port after the exterior valve is opened, and inserting the sleeve to a depth at which it forces open the interior valve, pushing the catheter tube through the sleeve into the through-passage and tracheal tube while maintaining the cover around said sleeve and catheter connecting the opposite end of the tube to a source of suction to remove matter from the tracheal tube during a time in which the plastic covering remains on the tube and the stop sleeve and thereafter removing the catheter tube with the stop sleeve by engaging the cover and without contaminating the surrounding area.

14. A method according to claim 13, wherein the catheter tube is covered by said plastic cover which engages around said stop sleeve at one end thereof and seals around the catheter tube at the other end thereof, said method further comprising pushing the catheter tube through the stop sleeve without removing the end thereof from the plastic covering.

15. A method according to claim 14, wherein the catheter tube includes a suction end having a connecting part and a separate tear-opening plastic covering said suction tube connecting part and wherein the plastic covering the suction tube connection part is torn off to connect the part to a source of suction, a plastic casing surrounding the stop sleeve is torn away to open the stop sleeve and permit its open end to be positioned in the connection.

\* \* \* \* \*